United States Patent
Yonamoto et al.

(10) Patent No.: US 9,018,954 B2
(45) Date of Patent: Apr. 28, 2015

(54) SAMPLE HOLDER FOR ELECTRICITY-DETECTION ELECTRON SPIN RESONANCE DEVICE

(75) Inventors: Yoshiki Yonamoto, Tokyo (JP); Naotoshi Akamatsu, Yokohama (JP)

(73) Assignee: Hitachi, Ltd., Tokyo (JP)

( * ) Notice: Subject to any disclaimer, the term of this patent is extended or adjusted under 35 U.S.C. 154(b) by 617 days.

(21) Appl. No.: 13/499,915

(22) PCT Filed: Oct. 1, 2010

(86) PCT No.: PCT/JP2010/005907
§ 371 (c)(1),
(2), (4) Date: May 24, 2012

(87) PCT Pub. No.: WO2011/043042
PCT Pub. Date: Apr. 14, 2011

(65) Prior Publication Data
US 2012/0223716 A1    Sep. 6, 2012

(30) Foreign Application Priority Data
Oct. 8, 2009  (JP) .................................. 2009-233979

(51) Int. Cl.
*G01V 3/00* (2006.01)
*G01R 33/30* (2006.01)
*G01N 24/10* (2006.01)
*G01R 33/60* (2006.01)

(52) U.S. Cl.
CPC ................ *G01R 33/30* (2013.01); *G01N 24/10* (2013.01); *G01R 33/60* (2013.01)

(58) Field of Classification Search
CPC ..................................................... G01R 33/20
USPC .......................................... 324/321, 318, 322
See application file for complete search history.

(56) References Cited

U.S. PATENT DOCUMENTS
4,887,037 A * 12/1989 Yajima et al. .................. 324/316
5,980,999 A * 11/1999 Goto et al. ..................... 427/572
(Continued)

FOREIGN PATENT DOCUMENTS
JP    5-157712    6/1993
JP    8-35919     2/1996
(Continued)

OTHER PUBLICATIONS
A. Maier et al., Electrically Detected Electron Spin Resonance (EDESR) in Thiophene Thin Films and a Thiophene/$C_{60}$ Double Layer, Solid State Communications, 1996, pp. 623-626, vol. 99, No. 9.
(Continued)

*Primary Examiner* — Louis Arana
(74) *Attorney, Agent, or Firm* — Baker Botts L.L.P.

(57) ABSTRACT

A sample holder structure is provided with which it is possible to reduce current noise derived from electromagnetic induction, etc. in electricity-detection electron spin resonance spectroscopy. Also provided is a process for producing the structure. The material of the sample holder, which is used in an electricity-detection electron spin resonance device, is an FR-4 resin, alumina, glass, or Teflon. The sample holder has four wiring leads formed on the surface thereof. The four wiring leads each has a three-layer structure composed of a nickel layer, a gold layer, and a resist layer which have been arranged in the order from the sample holder surface, and the sample holder has the shape of the letter T. The sample holder has, formed in the end thereof, a gold pad for affixing a sample, and the gold pad has a multilayer structure composed of a nickel layer and a gold layer arranged in this order from the sample holder surface. In the T-shaped head part of the sample holder, the four wiring leads are spaced wider from each other.

7 Claims, 4 Drawing Sheets

(56) References Cited

U.S. PATENT DOCUMENTS

| | | | |
|---|---|---|---|
| 6,917,201 B2* | 7/2005 | de Swiet | 324/321 |
| 2010/0206049 A1 | 8/2010 | Kasama et al. | |
| 2011/0193559 A1* | 8/2011 | Marumoto | 324/304 |

FOREIGN PATENT DOCUMENTS

| | | |
|---|---|---|
| JP | 11-312719 | 11/1999 |
| JP | 2001-28384 | 1/2001 |
| JP | 2008-39508 | 2/2008 |
| JP | 2009-47675 | 3/2009 |
| WO | WO 2008-140024 A1 | 11/2008 |

OTHER PUBLICATIONS

Toshiyuki Sato et al, "Ko Kando Denkiteki Kenshutsu ESR (EDMR) Sochi no Kaihatsu", Reports of Yamagata Research Institute of Technology, Mar. 1993, No. 30, pp. 31-33.

* cited by examiner

SAMPLE HOLDER FOR ELECTRICITY-DETECTION ELECTRON SPIN RESONANCE DEVICE

TECHNICAL FIELD

A conventionally existing electricity-detection electron spin resonance method is a kind of application of an electron spin resonance method. It is a method for evaluating a density and origins of defects in an insulating film in a sample having a layered structure of lower electrode-insulating film-upper electrode and characterized by being very sensitive. When a magnetic field is applied to a sample, orbitals of defects having unpaired electrons induce Zeeman splitting so that the orbital is split into two orbitals of a ground state and an excited state. In this stage, the unpaired electrons are present in the orbital of the ground state. When a microwave having energy equal to the width of Zeeman splitting is applied then, unpaired electrons present in the ground state absorb the microwave energy so as to transition into the excited state. As a voltage is applied between the lower electrode and the upper electrode so that a leakage current flows here, when the spin directions of the unpaired electrons in the defects and the electrons flowing in from the electrodes are parallel to each other, there occurs repulsion between the electrons. On the other hand, when the directions are anti-parallel, there is no repulsion between the electrons. For this reason, the leakage current depends on the directions of the unpaired electrons in the defects. When a magnetic field intensity is swept while a microwave with a constant wavelength is irradiated, the amount of the leakage current changes when absorption of the microwave occurs at a certain magnetic field intensity and the electron spins in the defects are reversed. The density of the defects can be evaluated based on the amount of the change of the leakage current and the origins of the defects can be evaluated based on the magnetic field intensities at which the amount of the leakage current changes. The problem here is measurement of the amount of the change of the leakage current. Generally, the change amount of the leakage current is so small to be less than or equal to $10^{-5}$ that it is detected using a lock-in amplifier but the measurement is still very difficult. Particularly, it is necessary to reduce current noise caused by electromagnetic induction.

As a sample holder for an electricity-detection spin resonance device, one which is disclosed in Patent Document 1 has been proposed.

CITATION LIST

Patent Literature

Patent Literature 1: JP-A-8-35919

SUMMARY OF INVENTION

Technical Problem

In order to detect a leakage current flowing in a sample with high sensitivity, it is necessary to reduce current noise originated from electromagnetic induction or the like as much as possible. However, an optimal method for it has not been established yet; it remains as a major problem of the electricity-detection electron spin resonance method. The present invention is to provide a structure of a sample holder which can reduce current noise originated from electromagnetic induction or the like in the electricity-detection electron spin resonance method.

Solution To Problem

The present invention is related to a sample holder for an electricity-detection electron spin resonance device for irradiating microwave and magnetic field intensity on and applying a voltage to a sample having an insulating film formed between a lower electrode and an upper electrode to thereby detect defects in the insulating film, including a sample holder substrate; wirings formed on the sample holder substrate; a pad connected to the wirings for connecting the lower electrode thereon; and a conductor connected to the wirings for connecting to the upper electrode.

Advantageous Effects of Invention

From the above, by using the present sample holder for electricity-detection electron spin resonance measurement it becomes possible to greatly reduce noise originated from electromagnetic induction so that a density and origins of defects in an insulating film can be evaluated.

BRIEF DESCRIPTION OF DRAWINGS

FIG. 3(*b*) is a graph showing a result of electricity-detection electron spin resonance measurement using a sample holder according to the present invention;

FIG. 4(*b*) is a diagram showing the configuration of the sample holder used in the case where the signal described in FIG. 4(*a*) is obtained.

DESCRIPTION OF EMBODIMENTS

Embodiment 1

Hereinafter, an embodiment of a sample holder in an electricity-detection electron spin resonance device according to the present invention is described specifically with reference to the drawings.

Figure 1:
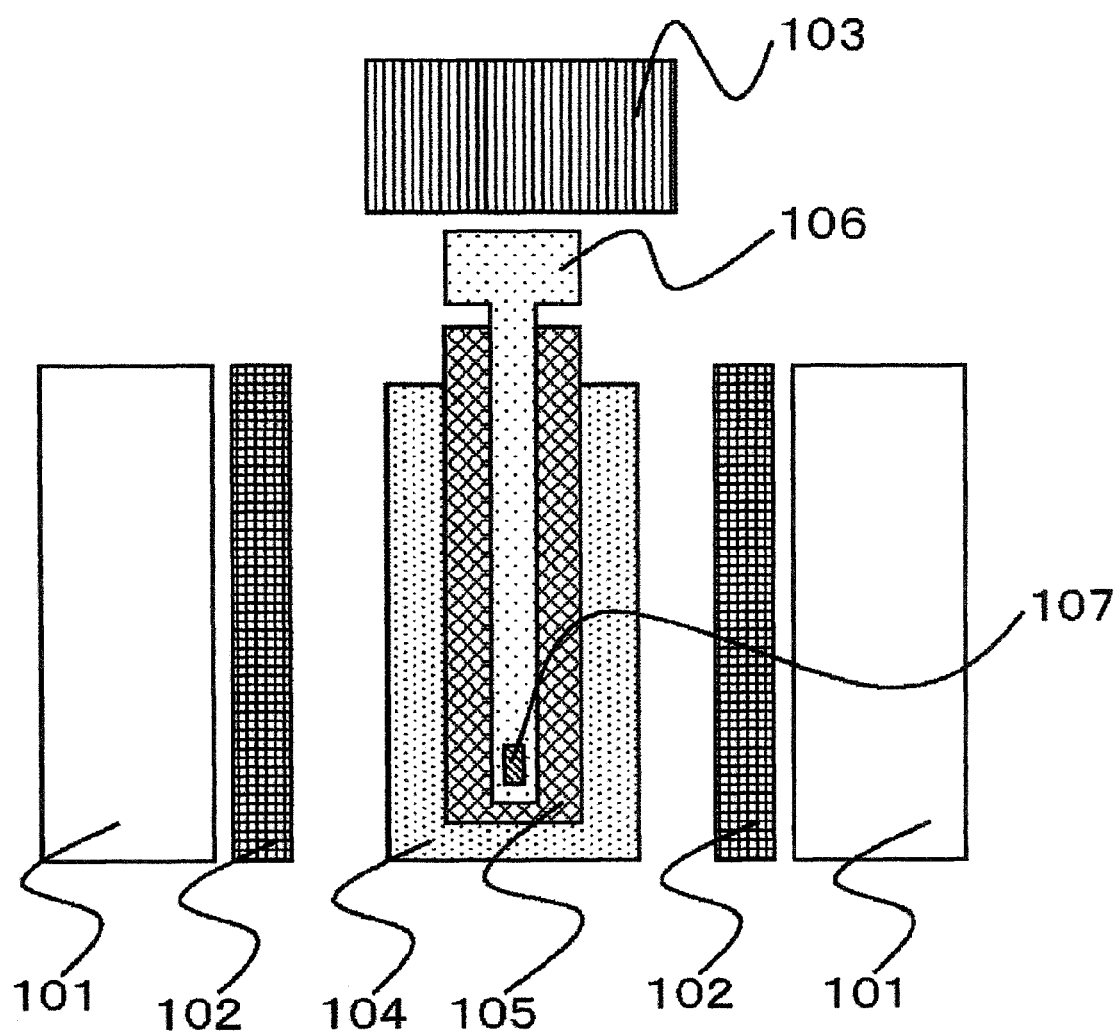
FIG. 1 is a schematic diagram showing an embodiment of an electricity-detection electron spin resonance measurement device using a sample holder associated with the present invention.

FIG. 1 is a schematic diagram of an electricity-detection electron spin resonance device. It comprises a DC magnetic field sweep electromagnet 101, an AC magnetic field application electromagnet 102, a microwave irradiation unit 103, a microwave resonance cavity 104, and a sample tube 105 installed into the microwave resonance cavity 104. A sample holder 106 and a measurement sample 107 are further inserted in the sample tube 105.

Next, the sample holder 106 used in the electricity-detection electron spin resonance device in the present invention is described.

Figure 2:
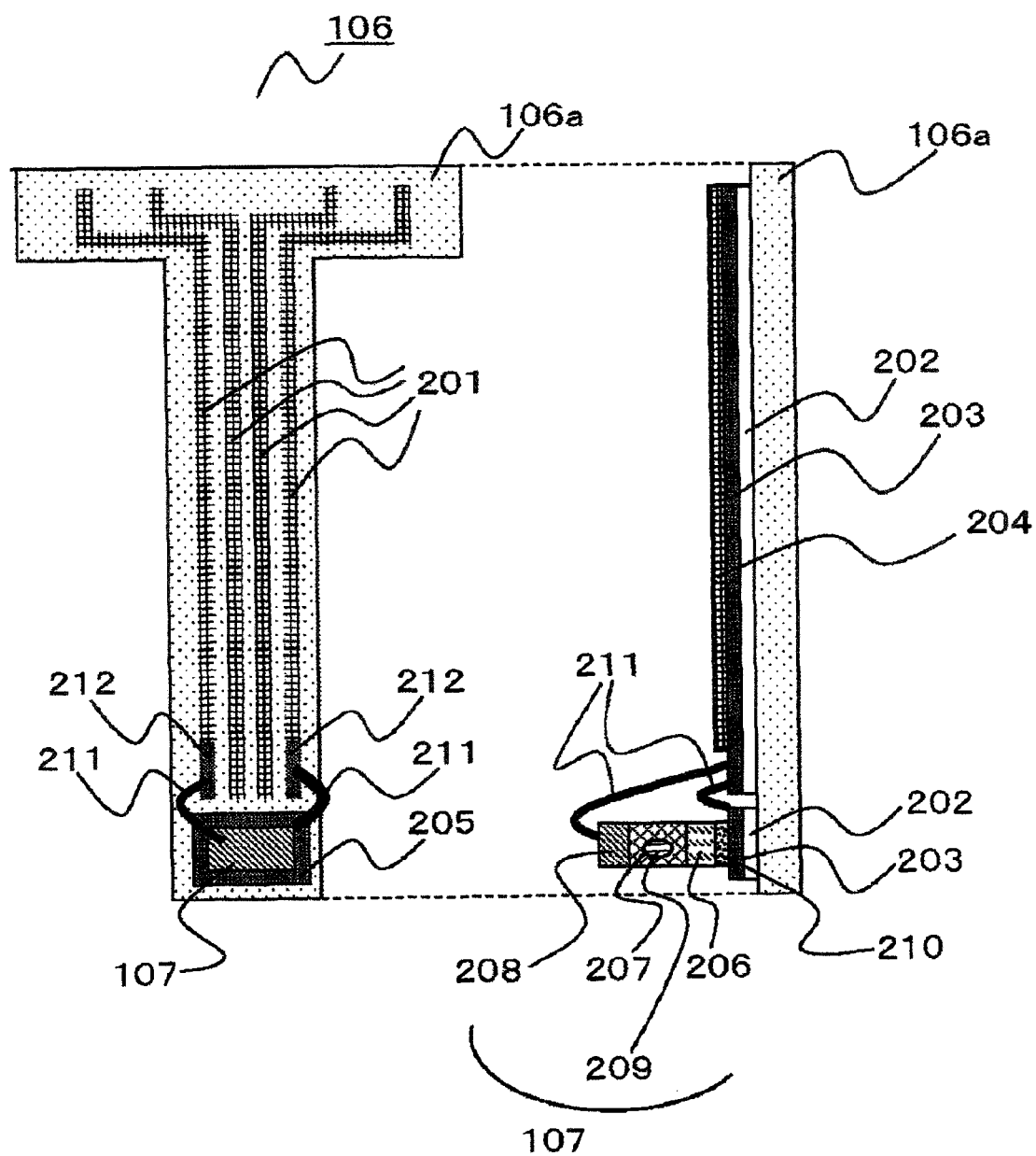
FIG. 2 is a diagram showing a structure of a sample holder according to the present invention.

As shown in FIG. 2, a substrate 106*a* of the sample holder 106 is T-shaped and four wirings 201 are formed on its surface. Here, material of the sample holder substrate 106*a* is any one of FR-4 resin, alumina, Teflon (registered trademark), and glass. The four wirings 201 have a layered structure with three layers of nickel 202, gold 203, and resist 204 from the surface of the sample holder. A gold pad 205 for holding the sample is formed at a tip of the sample holder 106 and its structure is a layered structure of nickel 202 and gold 203 from the surface of the sample holder substrate 106a. The measurement sample 107 has a structure of lower electrode 206—insulating film 207—upper electrode 208 such as gold-silicon oxide film-gold, for example, and a defect 209 having unpaired electrons is present in the insulating film 207. The lower electrode 206 of the measurement sample 107 is connected to the gold pad 205 by a conductive adhesive 210 such as silver paste. Further, the gold pad 205 is connected to a spot 212 of a wiring out of the four wirings 201, where the resist 204 is removed, by a fine wire 211 of conductive material such as gold or aluminum. A fine wire 211 is also connected to the upper electrode 208 in the same manner.

Here, the wiring spacings among the four wirings 201 in a head portion (a portion with a greater width) of the T-shape of the sample holder 106 are set to be larger than the wiring spacings in the other portion. This is, because noise caused by electromagnetic induction becomes large when the distance between the wirings is small, to mitigate this influence. Moreover, two of the four wirings 201 located inside are grounded in order to reduce the noise caused by electromagnetic induction. The reason why the number of grounded wirings is two is described. The noise reduction effect is greater as the distance between a grounded wiring and a wiring through which a measurement signal flows is closer. However, by making the number of grounded wirings to be one and setting the distance between the grounded wiring and a wiring through which a signal flows to be short, the distance between wirings through which signals flow also becomes short and noise is generated by interaction. Therefore, when the number of grounded wirings is two, the distance between a grounded wiring and a signal wiring can be shortened to reduce noise while the distance between the signal wirings is secured.

Besides, as the material of the sample holder substrate 106a, use of any one of the aforementioned four kinds (FR-4 resin, alumina, Teflon and glass) is necessary. This is because with other materials (such as PCB (polycarbonate) resin) microwave absorption which causes noise is large.

Moreover, with respect to the four wirings 201, nickel 202 is inserted between with the sample holder substrate 106a to prevent the gold 203 from being peeled off when the fine wires 211 are formed by a wire bonding method or the like. Whereas nickel is good in adhesion to the substrate 106a, its conductivity is not as good as gold and, because nickel is a magnetic substance, there are such disadvantages that the sample position may change by being subjected to a force due to a magnetic field or that noise tends to be generated. Therefore, by adopting a layered structure of the thin nickel 202 and the gold 203 thicker than the nickel 202 from the side of the substrate 106a, the drawbacks to nickel 202 can be suppressed and continuity can be made with low noise by gold 203 while adhesion of the substrate 106a to the wirings 201 is secured. Although gold 203 is selected here as a material of good adhesion to the fine wires 211, there is no obstacle to the present invention even when other material of good adhesion is used. Besides, in a state where the gold 203 is exposed, noise due to electromagnetic induction is large. To mitigate this influence, the resist 204 is formed over the gold 203. Since the resist 204 is an insulating substance having no conductivity, however, it is necessary to form the spots 212 where parts of the resist 204 are removed as the fine wires 211 are connected. At the gold pad 205 gold is formed wider than the wirings 201 and it is a place necessary for electrically connecting the lower electrode 206 with the adhesive 210.

Next, a procedure of performing electricity-detection electron spin resonance measurement using the sample holder 106 in the present invention is described specifically.

Figure 3A:
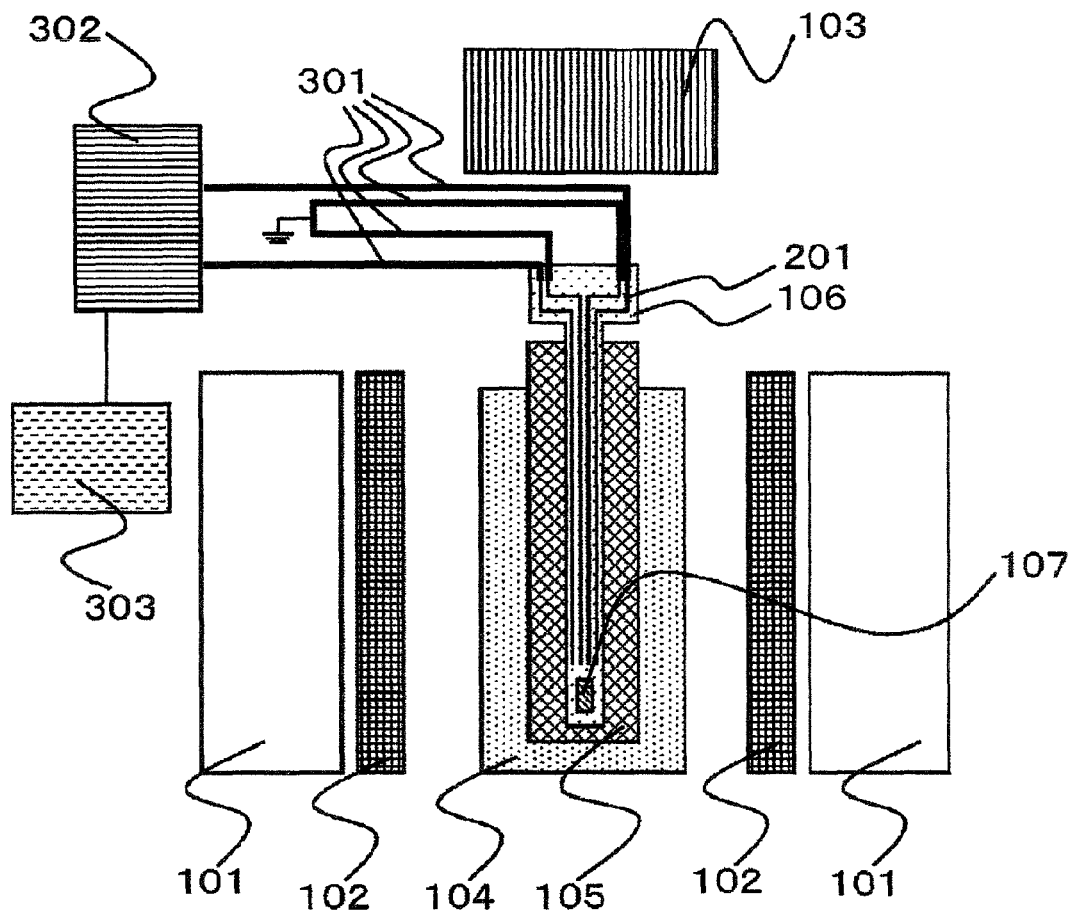
FIG. 3(*a*) is a diagram for explaining an embodiment when electricity-detection electron spin resonance measurement is performed using a sample holder according to the present invention.
Figure 3B:
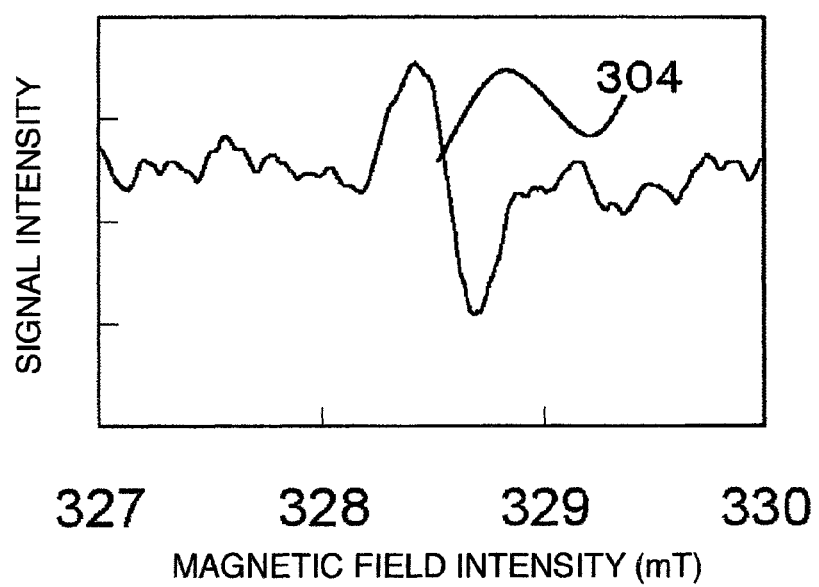

FIG. 3(a) is a diagram showing an experimental procedure of an electricity-detection electron spin resonance experiment. Cables 301 are extended from the wirings 201 on the sample holder 106 equipped with the measurement sample 107 and are connected to a power supply/ammeter 302. Description is given here with an example of a structure having the lower electrode 206 of gold, the insulating film 207 of a 1 nm-thick silicon oxide film, and the upper electrode 208 of gold as the measurement sample 107; there is no impediment to the present invention even when material of the upper and lower electrodes or the insulating film is changed. Here, a DC magnetic field of 327 mT to 330 mT is applied to and swept on the sample 107 by the DC magnetic field sweep electromagnet 101. At the same time, an AC magnetic field of an amplitude of 0.5 mT and a frequency of 80 Hz is applied by the AC magnetic field electromagnet 102. Moreover, a microwave of a fixed frequency of 9.6 MHz is irradiated on the measurement sample 107 using the microwave irradiation unit 103 for this state. From the power supply/ammeter 302 a voltage of 0.5V is applied between the lower electrode 206 and the upper electrode 208 of the measurement sample 107. Then, the amount of the change of the leakage current on this occasion is detected using an lock-in amplifier 303 and plotted with respect to the intensity of the swept DC magnetic field to be able to obtain a signal 304 as shown in FIG. 3(b). Incidentally, the similar signal can be obtained even when the sweep range of the DC magnetic field, the amplitude and the frequency of the AC magnetic field, the microwave frequency, or the voltage value applied to the measurement sample 107 is changed here and there is no influence on the present invention.

Next, the effect of the sample holder 106 of the present invention is described with reference to FIG. 4.

Figure 4A:
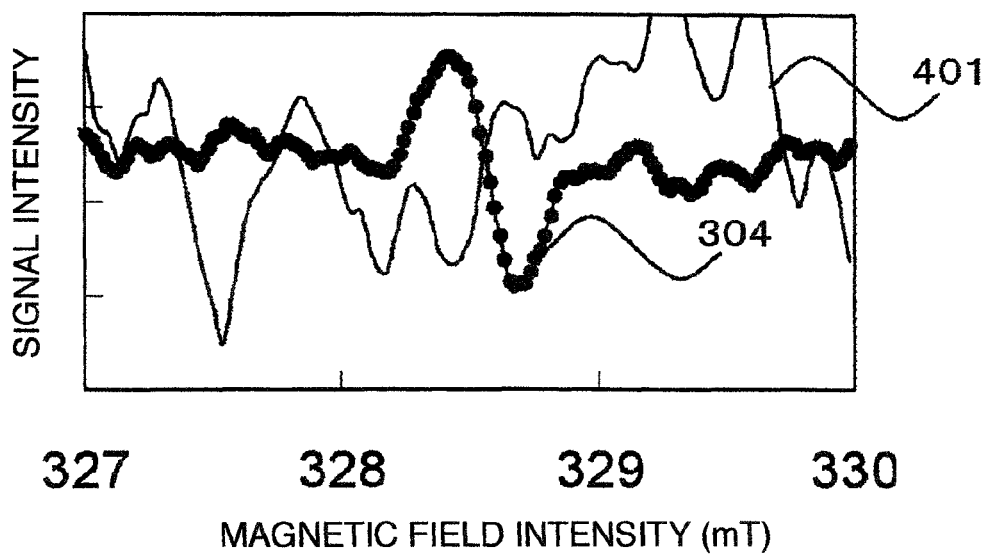
FIG. 4(*a*) is a graph describing signals obtained in electricity-detection electron spin resonance measurement in the case where a sample holder according to the present invention is used and in the case where a sample holder shown in FIG. 4(*b*) is used.
Figure 4B:
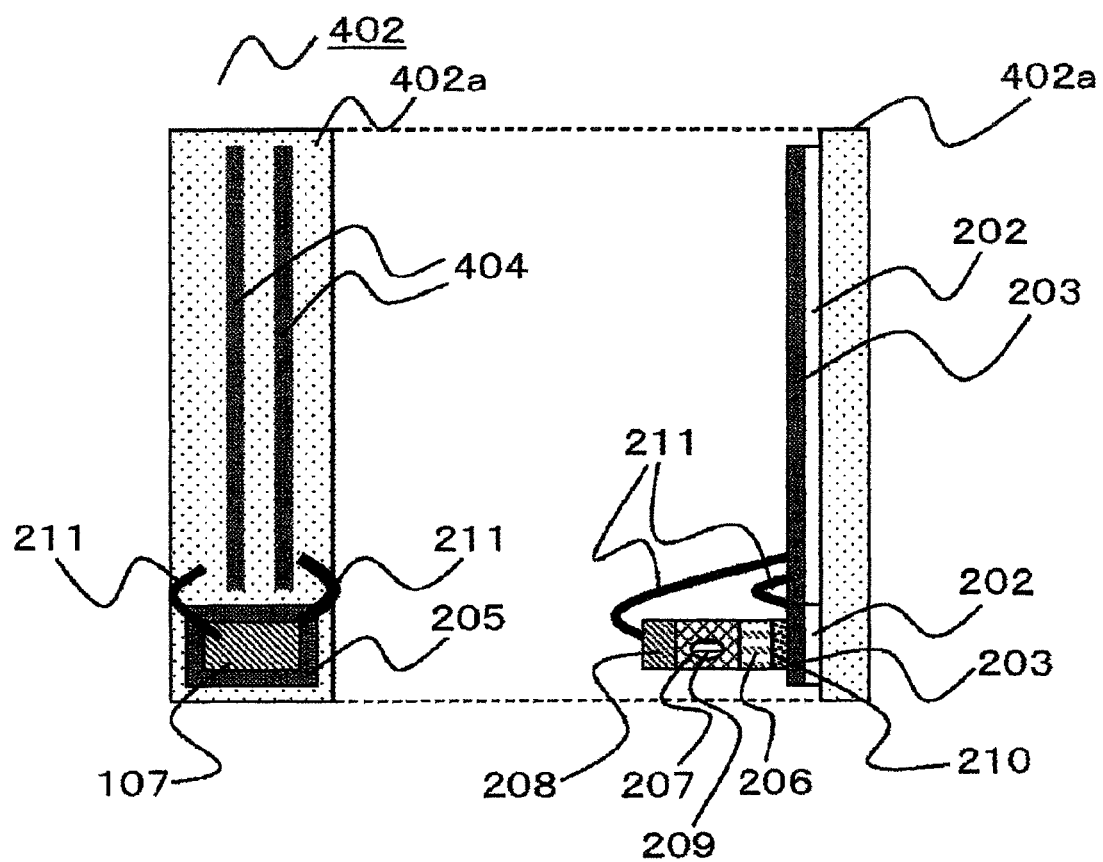

FIG. 4(a) is the signal 304 of the electricity-detection electron spin resonance measured using the sample holder 106 of the present invention. On the other hand, a signal 401 is a result of measurement using a sample holder 402 shown in FIG. 4(b). Here, as for the signal 401 values scaled down to a ten-thousandth are shown. In the sample holder 402, the number of wirings 404 is two and there is no coating with the resist 204. Besides, FR-4 resin is used as the material of a substrate 402a. Moreover, because unlike the sample holder 106 it is not T-shaped, the spacing between the wirings 404 is the same distance everywhere on the holder 402. While noise in the signal 401 is so large that measurement is difficult, noise in the signal 304 is greatly reduced. It is evaluated from the value of DC magnetic field intensity generating the signal 304 that the origin of the present defect 209 is oxygen deficiency, and from the intensity of the signal 304 that the density of the defect 209 is $9 \times 10^{-8}/cm^2$. Also, while the size of S/N is about 10 with the sample holder 106 of the present invention, it is equal to or less than 0.001 when the sample holder 402 is used. The effect of the present sample holder is verified from this result.

REFERENCE SIGNS LIST

101 . . . DC magnetic field sweep electromagnet, 102 . . . AC magnetic field application electromagnet, 103 . . . microwave irradiation unit, 104 . . . microwave resonance cavity, 105 . . . sample tube, 106 . . . sample holder, 106a . . . sample holder substrate, 107 . . . measurement sample, 201 . . . four wirings, 202 ... nickel, 203 ... gold, 204 ... resist, 205 ... gold pad, 206 ... lower electrode, 207 ... insulating film, 208 ... upper electrode, 209 ... defect, 210 ... adhesive, 211 ... fine wires, 212 ... spots where the resist 204 is removed, 301 ... cables, 302 ... power supply/ammeter, 303 ... lock-in amplifier, 304 ... signal, 401 ... signal, 402 ... sample holder.

The invention claimed is:

1. A sample holder for an electricity-detection electron spin resonance device for irradiating microwave and magnetic field intensity on and applying a voltage to a sample having an insulating film formed between a lower electrode and an upper electrode to thereby detect defects in the insulating film comprising:
    a sample holder substrate;
    wirings formed on the sample holder substrate;
    a pad connected to the wirings for connecting the lower electrode thereon; and
    a conductor connected to the wirings for connecting to the upper electrode.

2. A sample holder for an electricity-detection electron spin resonance device according to claim 1, further comprising four wirings formed side by side on a surface of the sample holder substrate; wherein outer two of the four wirings are connected to the pad and the conductor and inner two of the four wirings are grounded.

3. A sample holder for an electricity-detection electron spin resonance device according to claim 1, wherein material of the sample holder substrate is FR-4 resin, alumina, glass, or Teflon.

4. A sample holder for an electricity-detection electron spin resonance device according to claim 2, wherein the four wirings are configured of a three-layer structure of nickel, gold, and resist from the surface of the sample holder substrate.

5. A sample holder for an electricity-detection electron spin resonance device according to claim 1, wherein the sample holder substrate is of a T-shape and the pad where the sample is mounted is formed near a tip of a narrow width side of the T-shape.

6. A sample holder for an electricity-detection electron spin resonance device according to claim 5, wherein the pad is configured of a layered structure of nickel and gold from the surface of the sample holder substrate.

7. A sample holder for an electricity-detection electron spin resonance device according to claim 5, wherein spacings between the four wirings in a head portion of the T-shape of the sample holder are wider than those in the other portion and a connecting portion of the wirings and a device outside the holder is formed in the head portion of the T-shape.

* * * * *